(12) United States Patent
Fujita et al.

(10) Patent No.: US 11,395,598 B2
(45) Date of Patent: Jul. 26, 2022

(54) PULSE WAVE DETECTION DEVICE AND BIOLOGICAL INFORMATION MEASURING DEVICE

(71) Applicant: OMRON HEALTHCARE CO., LTD., Kyoto (JP)

(72) Inventors: Reiji Fujita, Muko (JP); Shingo Yamashita, Muko (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 322 days.

(21) Appl. No.: 16/158,495

(22) Filed: Oct. 12, 2018

(65) Prior Publication Data

US 2019/0038139 A1    Feb. 7, 2019

Related U.S. Application Data

(63) Continuation of application No. PCT/JP2017/012701, filed on Mar. 28, 2017.

(30) Foreign Application Priority Data

Apr. 13, 2016 (JP) .............................. JP2016-080321

(51) Int. Cl.
*A61B 5/022* (2006.01)
*A61B 5/02* (2006.01)
(Continued)

(52) U.S. Cl.
CPC ............... *A61B 5/022* (2013.01); *A61B 5/02* (2013.01); *A61B 5/02141* (2013.01); *A61B 5/6824* (2013.01); *A61B 2560/0406* (2013.01)

(58) Field of Classification Search
CPC ....... A61B 5/022; A61B 5/02; A61B 5/02141; A61B 5/6824; A61B 2560/0406; A61B 5/02438; A61B 5/681; A61B 5/6831
See application file for complete search history.

(56) References Cited

U.S. PATENT DOCUMENTS 5,179,956 A * 1/1993 Harada .............. A61B 5/02233
                                                       600/485
5,240,007 A   8/1993 Pytel et al.
(Continued)

FOREIGN PATENT DOCUMENTS

EP    1 308 105    5/2003
EP    1 338 214    8/2003
(Continued)

OTHER PUBLICATIONS

International Search Report dated Jun. 6, 2017 in International (PCT) Application No. PCT/JP2017/012701 with English translation.

(Continued)

*Primary Examiner* — Devin B Henson
*Assistant Examiner* — Justin Xu
(74) *Attorney, Agent, or Firm* — Wenderoth, Lind & Ponack, L.L.P.

(57) ABSTRACT

A pulse wave detector includes a body portion; a band which is wound around a wrist while the band is engaged with the body portion; a first engaging portion with which a basal end portion in a longitudinal direction of the band is engaged; a second engaging portion with which an arbitrary position in the longitudinal direction of the band is engaged while the band is folded back; and an engagement member which causes a tip end portion in the longitudinal direction of the band to be engaged with the basal end portion or the first end portion while the basal end portion and the tip end portion overlap with each other. A tip end of the tip end portion is directed from an opposed surface of the body portion to the wrist to an opposite surface of the body portion.

6 Claims, 7 Drawing Sheets

(51) Int. Cl.
    *A61B 5/021*     (2006.01)
    *A61B 5/00*     (2006.01)
    *A61B 5/024*     (2006.01)

(56) References Cited

U.S. PATENT DOCUMENTS

| 5,830,149 A | 11/1998 | Oka et al. |
| 2005/0234351 A1 | 10/2005 | Nishii et al. |

FOREIGN PATENT DOCUMENTS

| JP | 06-507563 | 9/1994 |
| JP | 08-256998 | 10/1996 |
| JP | 2002-224098 | 8/2002 |
| JP | 2004-129979 | 4/2004 |
| JP | 2005-324004 | 11/2005 |
| JP | 2014-018357 | 2/2014 |

OTHER PUBLICATIONS

Written Opinion of the International Searching Authority dated Jun. 6, 2017 in International (PCT) Application No. PCT/JP2017/012701.

Office Action dated Oct. 10, 2020 in corresponding Chinese Patent Application No. 201780023344.6, with Machine translation.

\* cited by examiner

PULSE WAVE DETECTION DEVICE AND BIOLOGICAL INFORMATION MEASURING DEVICE

CROSS-REFERENCE TO RELATED APPLICATIONS

This is a Continuation of International Patent Application No. PCT/JP2017/012701 filed Mar. 28, 2017, which claims the benefit of Japanese Patent Application No. 2016-080321 filed Apr. 13, 2016. The disclosures of the prior applications are hereby incorporated by reference herein in their entireties.

TECHNICAL FIELD

Aspects of the present invention relate to a pulse wave detector and a biometric information measurement device.

BACKGROUND ART

A biometric information measurement device is known that, in a state where a pressure sensor is directly contacted with a living body portion through which an artery such as the radial artery in the wrist passes, can measure biometric information such as the pulse rate or the blood pressure by using a pressure pulse wave detected by the pressure sensor (for example, see Patent Literature 1 (JP-A-H8-256998), Patent Literature 2 (JP-A-2002-224098) and Patent Literature 3 (JP-T-H6-507563)).

A blood pressure measurement device disclosed in Patent Literature 1 calculates a blood pressure vale by using a cuff in a portion different from a living body portion with which a pressure sensor is contacted, and produces calibration data from the calculated blood pressure value. Then, the blood pressure measurement device calibrates a pressure pulse wave detected by a pressure pulse wave sensor which is attached to the wrist, with the calibration data, thereby calculating the blood pressure value for every pulse. The pressure pulse wave sensor has a configuration where the sensor is accommodated in a housing, and the housing is secured to the wrist with a band.

Each of pressure pulse wave sensors disclosed in Patent Literatures 2 and 3 has a housing which accommodates a pressure detecting element, and a band in which a basal end portion is engaged with the housing. The pressure pulse wave sensor is attached to the wrist of a measurement subject by causing the band to be wound around the wrist in a state where the housing is placed so that the pressure detecting element is opposed to an artery in the wrist, and a tip end portion of the band to be engaged with the housing.

Pulse wave detectors that attach to the wrist, and detect a pulse wave from an artery in the wrist, such as those exemplified in Patent Literatures 1 to 3, are required to have superior attachability to the wrist, and accuracy of positional alignment between a pulse wave detecting section and the artery.

In the pressure pulse wave sensor disclosed in Patent Literature 2, the band is once folded back in a ring disposed in a portion of the housing on the side of the ulna, from the palm of the measurement subject toward the back of the hand, and a tip end portion of the folded back band is pulled toward the back of the hand. Then, the sensor is attached to the wrist by coupling the pulled tip end portion to a hook and loop fastener disposed on the band. In the configuration where attachment is performed by pulling the tip end portion of the band from the palm side of the measurement subject toward the back of the hand as described above, the measurement subject needs to be accustomed to attachment.

In the pressure pulse wave sensor disclosed in Patent Literature 2, a procedure is assumed in which the measurement subject places the arm on a table so that the back of the hand is opposed to the table, then the housing is placed so that the pressure detecting element is opposed to the radial artery, and thereafter the band is fastened. In the procedure, when the band is to be fastened, the measurement subject needs to perform an operation of slightly raising the arm. Therefore, there is a possibility that this operation may cause positional displacement of the pressure detecting element with respect to the radial artery.

When the wrist of the measurement subject is divided into halves in a direction perpendicular to the running direction of the radial artery, the pressure detecting element is placed on the side of the thumb of the measurement subject. When the band is to be fastened, the tip end portion of the band which is folded back in the ring that is disposed on the side of the little finger of the measurement subject is pulled toward the palm. Therefore, there is a possibility that a force which is applied to the wrist when the band is pulled acts more strongly on the side of the little finger than on the thumb side, and positional displacement of the pressure detecting element that is placed on the side of the thumb may be caused.

In the pressure pulse wave sensor disclosed in Patent Literature 3, the sensor is attached to the wrist by pulling a tip end portion of the band engaged with the housing from the back of the hand of the measurement subject toward the palm, and causing the tip end portion to engaging with the housing. Therefore, the above-discussed problems with respect to Patent Literature 2 can be solved. In the band structure disclosed in Patent Literature 3, the band is singly wound around the wrist of the measurement subject. Therefore, the attachment stability is low, and there is a possibility that, after attachment, positional displacement of the pulse wave detecting section may occur.

Patent Literature 1 fails to specifically describe the manner of winding the band around the wrist to secure the pressure pulse wave sensor to the wrist. Although, here, the problems of the devices for detecting a pressure pulse wave from the radial artery have been described, similar problems occur also in a device or the like which detects a pulse wave from the radial artery by using, for example, a photoelectric sensor.

SUMMARY

Embodiments of the present invention address the above disadvantages and other disadvantages not described above. However, the present invention is not required to overcome the disadvantages described above, and thus, an exemplary embodiment of the present invention may not overcome any of the problems described above.

A pulse wave detector according to an embodiment of the present invention is used while being attached to a wrist of a measurement subject and includes: a body portion which includes a detecting section configured to detect a pulse wave from a radial artery of the measurement subject; a band which is configured to be wound around the wrist in a state where the band is engaged with the body portion, so as to maintain a state where the detecting section is opposed to the radial artery a first engaging portion which is disposed on a first end portion that is one of end portions of the body portion on a side of an ulna of the wrist in a circumferential direction of the wrist, and with which a basal end portion in a longitudinal direction of the band is engaged; a second engaging portion which is disposed on a second end portion that is one of the end portions of the body portion on a side of a radius of the wrist in the circumferential direction, and with which an arbitrary position in the longitudinal direction of the band engaged with the first engaging portion is engaged in a state where the band is folded back in a direction to be separated from the body portion; and an engagement member which is configured to cause a tip end portion in the longitudinal direction of the band to be engaged with the basal end portion or the first end portion in a state where the basal end portion engaged with the first engaging portion and the tip end portion of the band engaged with the second engaging portion overlap with each other, wherein the tip end portion is engaged with the basal end portion or the first end portion through the engagement member in a state where a tip end of the tip end portion is directed from a side of an opposed surface of the body portion to the wrist, to a side of a surface of the body portion which is opposite to the opposed surface.

A biometric information measurement device according to an embodiment of the present invention includes the above pulse wave detector; and a biometric information calculating section which is configured to calculate biometric information based on the pulse wave detected by the detecting section.

BRIEF DESCRIPTION OF DRAWINGS

The above and other aspects of the present invention will become more apparent and more readily appreciated from the following description of embodiments of the present invention taken in conjunction with the attached drawings.

DESCRIPTION OF EMBODIMENTS

Hereinafter, embodiments of the present invention will be described with reference to the drawings.

Figure 1:
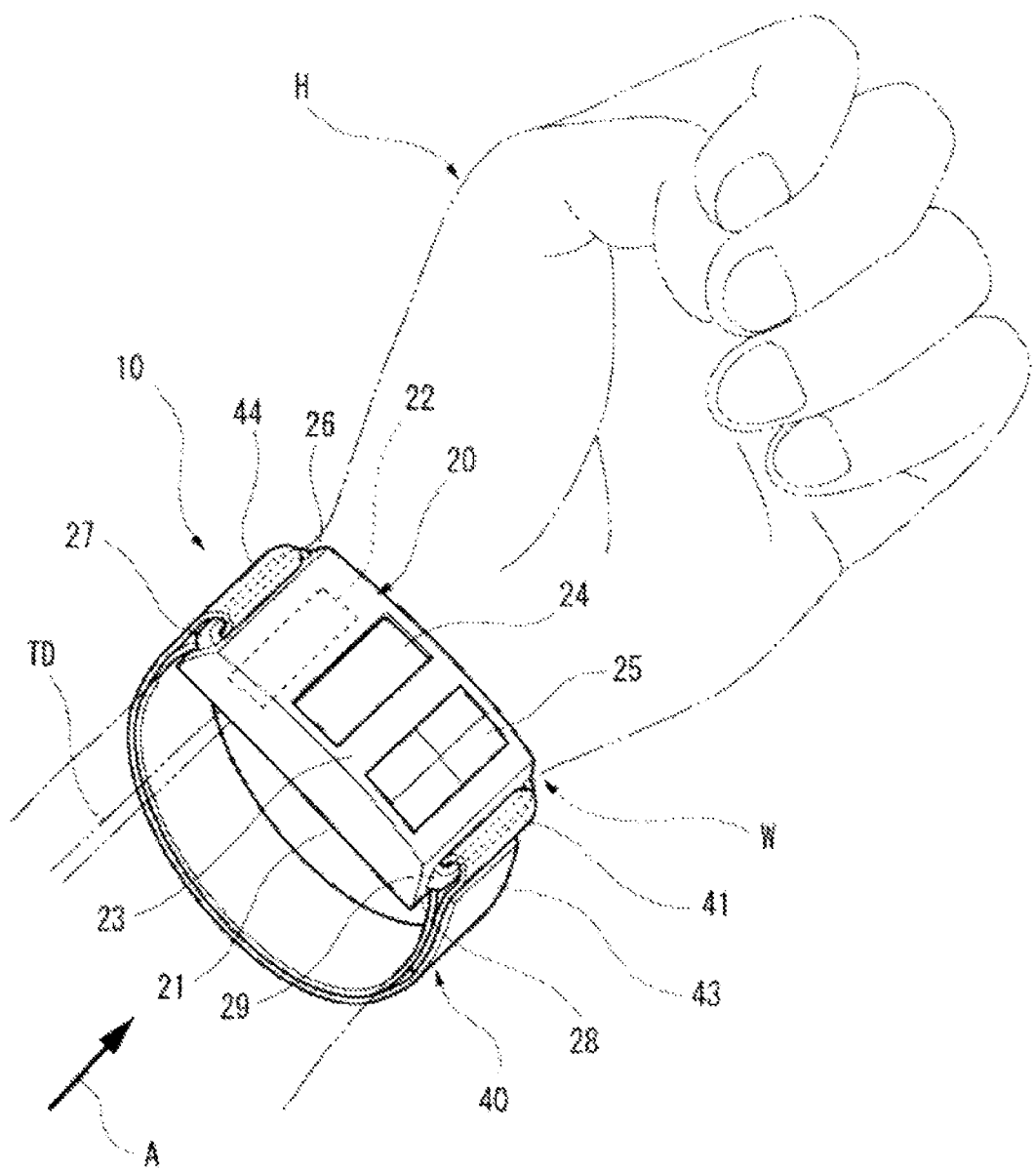
FIG. 1 is a perspective view schematically showing the external configuration of a biometric information measurement device 10 of a first embodiment of the present invention.
Figure 2:
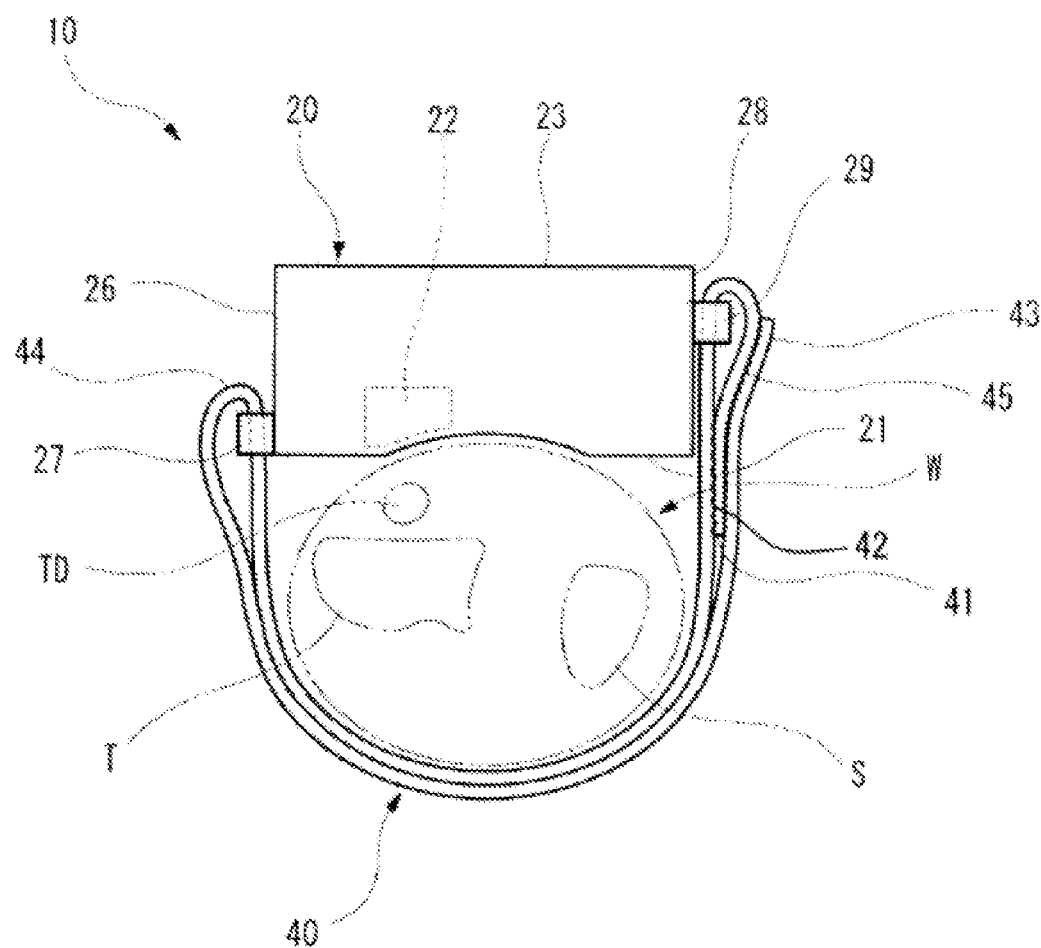
FIG. 2 is a side view of the biometric information measurement device 10 shown in FIG. 1, as seen from the side of the elbow of the left hand of a measurement subject.

FIG. 1 is a perspective view schematically showing the external configuration of a biometric information measurement device 10 of a first embodiment of the present invention. As shown in FIG. 1, the biometric information measurement device 10 is used while being attached to the wrist W of the left hand H of a measurement subject. FIG. 2 is a side view of the biometric information measurement device 10 shown in FIG. 1, as seen from the side (the direction A in FIG. 1) of the elbow of the left hand H of the measurement subject.

The biometric information measurement device 10 has: a housing 20 which constitutes a body portion including a pulse wave detecting section 22 that can detect a pulse wave (a pressure pulse wave or a volume pulse wave) from the radial artery TD extending along the radius T in the wrist W of the measurement subject, and which is formed of a metal or a resin; a band 40 which is engaged with the housing 20.

The pulse wave detecting section 22 may have a known configuration. For example, the pulse wave detecting section 22 has a pressure sensor, and a mechanism which presses it against the skin, and detects a pressure pulse wave by using the pressure sensor. Alternatively, the pulse wave detecting section 22 has a photoelectric sensor, and detects a volume pulse wave from a signal detected by the photoelectric sensor.

In the example of FIG. 1, the housing 20 is a member having an approximately box-like shape, and includes the pulse wave detecting section 22, and a biometric information calculating section (not shown) which calculates biometric information such as the heart rate, the pulse rate, or the blood pressure value based on the pulse wave detected by the pulse wave detecting section 22.

The biometric information calculating section may be disposed in an apparatus other than the biometric information measurement device 10. Namely, the housing 20 of the biometric information measurement device 10 may need to have at least the pulse wave detecting section 22. In this case, the biometric information measurement device 10 functions as the pulse wave detector.

The surface (the surface opposed to the wrist W) of the housing 20 which, in the case where the biometric information measurement device 10 is attached to the wrist W, is opposed to the wrist W constitutes a detection surface 21. The detection surface 21 may have an approximately flat shape, or a part or the whole of the surface may be arcuate so as to extend along the outer shape of the wrist W. The pulse wave detecting section 22 is disposed in a position which is opposed to the radial artery TD in a state where the detection surface 21 is opposed to the wrist W.

In the housing 20, the surface (the opposite surface) opposite to the detection surface 21 constitutes a display surface 23. In the display surface 23, a displaying portion 24 configured by a liquid crystal display device or the like for displaying measurement results, and an operating section 25 for operating the biometric information measurement device 10 are disposed. The positions where the displaying portion 24 and the operating section 25 are respectively disposed are not limited to those shown in FIG. 1. A configuration where the displaying portion 24 is omitted may be employed.

A first engaging portion 29 is disposed on a first end portion 28 (in the example of FIGS. 1 and 2, an end surface of the housing 20 on the side of the ulna S) which is one of end portions of the housing 20 on the side of the ulna S in the circumferential direction of the wrist W. The first engaging portion 29 is disposed on the first end portion 28, and on the side of the display surface 23. Namely, the first engaging portion 29 is disposed on a part which is in the first end portion 28, and which is on the side that is close to the display surface 23 in the case where the housing 20 is divided into halves in a direction perpendicular to the display surface 23. Alternatively, the first engaging portion 29 may be disposed on the first end portion 28, and on the side of the detection surface 21.

A second engaging portion 27 is disposed on a second end portion 26 (in the example of FIGS. 1 and 2, an end surface of the housing 20 on the side of the radius T) which is one of end portions of the housing 20 on the side of the radius T in the circumferential direction of the wrist W.

The first engaging portion 29 and the second engaging portion 27 are used for causing the band 40 to engage with the housing 20. Each of the first engaging portion 29 and the second engaging portion 27 has a shape that has a hole portion into which the band 40 can be inserted.

Figure 3:
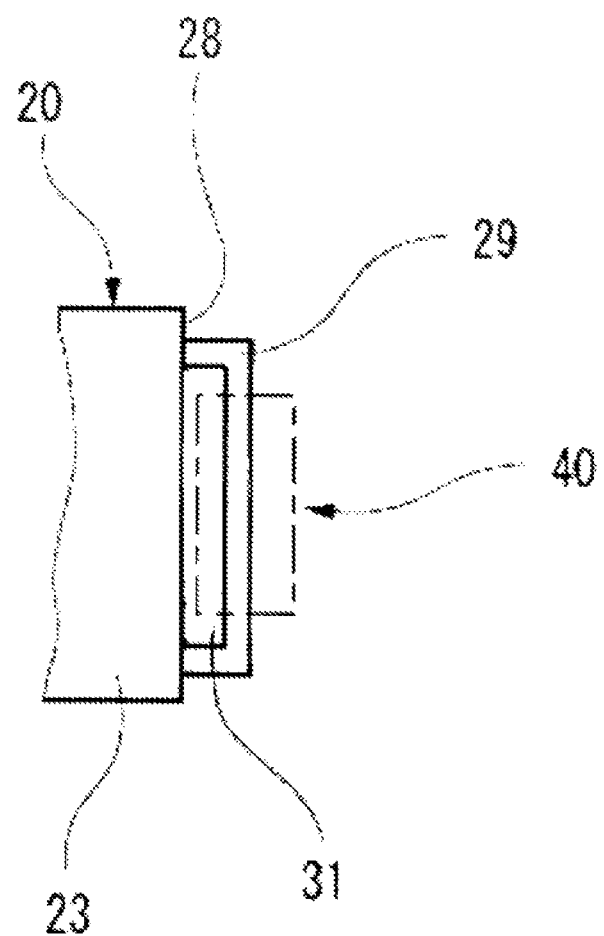
FIG. 3 is a view of the vicinity of a first engaging portion 29 of the biometric information measurement device 10 shown in FIG. 2, as seen from the side of a display surface 23 of a housing 20.

FIG. 3 is a view of the vicinity of the first engaging portion 29 of the biometric information measurement device 10 shown in FIG. 2, as seen from the side of the display surface 23 of the housing 20.

As shown in FIG. 3, the first engaging portion 29 is configured by a member which is erected from the first end portion 28 of the housing 20, and which has a shape approximately similar to a Greek character Π, and a hole portion 31 is formed between this member and the first end portion 28 of the housing 20. The band 40 can be inserted into the hole portion 31. The second engaging portion 27 is configured in a similar manner to the first engaging portion 29.

The first engaging portion 29 may need to be disposed on the first end portion 28, and may be disposed on the display surface 23 of the first end portion 28, on the detection surface 21 of the first end portion 28, or the like.

The second engaging portion 27 may need to be disposed on the second end portion 26, and may be disposed on the display surface 23 of the second end portion 26, on the detection surface 21 of the second end portion 26, or the like.

The band 40 is configured to be wound around the wrist W in a state where one end is engaged with the housing 20 (routed so as to form a state where the wrist W is sandwiched between the band 40 and the housing 20), so as to maintain the state where the pulse wave detecting section 22 is opposed to the radial artery TD.

For example, the band 40 is a strip-like member which is lower in rigidity than the housing 20. As the material of the band 40, for example, cloth, leather, rubber, thin resin, or the like may be used. Therefore, the band 40 can be easily folded back.

A basal end portion 41 which constitutes one end of the band 40 in the longitudinal direction is detachably engaged with the first engaging portion 29 which is disposed on the first end portion 28.

Specifically, the basal end portion 41 of the band 40 is inserted into the hole portion 31 of the first engaging portion 29, in a direction from the side of the detection surface 21 toward the display surface 23. The basal end portion 41 which has passed through the hole portion 31 is folded back in an approximately U-like shape in a direction to be separated from the housing 20. A hook and loop fastener 42 is formed on the surface of the non-folded back part of the basal end portion 41 and directed in the direction opposite to the housing 20, and the surface of the folded back part of the basal end portion 41 and directed to the housing 20. Because of the hook and loop fastener 42, the folded back part of the basal end portion 41 is detachably engaged with the band 40.

The hook and loop fastener 42 is an engagement member for causing the basal end portion 41 to detachably engage with the band 40. Incidentally, a configuration may be employed where, in the state shown in FIG. 2, a convex portion or concave portion which is disposed on the surface of the folded back part of the basal end portion 41 and directed to the housing 20 is fitted into a concave portion or convex portion which is disposed on the surface of the non-folded back part of the basal end portion 41 and directed in the direction opposite to the housing 20, whereby the basal end portion 41 is detachably engaged with the band 40.

In this case, the concave portion and the convex portion constitute the engagement member. Alternatively, the non-folded back part and folded back part of the basal end portion 41 may be completely secured to each other by an adhesive agent, sewing, or the like. Namely, the basal end portion 41 may be non-detachably engaged with the first engaging portion 29.

An arbitrary position 44 between the basal end portion 41 of the band 40 which is engaged with the first engaging portion 29, and a tip end portion 43 which is the end portion that is opposite in the longitudinal direction to the basal end portion 41 of the band 40 is engaged in the state where the band is folded back in a direction to be separated from the housing 20, in the second engaging portion 27 that is disposed on the second end portion 26 of the housing 20.

Specifically, in the band 40 which is engaged with the first engaging portion 29, the tip end portion 43 is inserted into the hole portion of the second engaging portion 27 from the side of the detection surface 21 toward the display surface 23. The band 40 which is inserted into the hole portion of the second engaging portion 27 is folded back in the arbitrary position 44 in an approximately U-like shape in a direction to be separated from the housing 20. In the state where the tip end portion 43 of the folded back band 40 overlaps with the first end portion 28 in the circumferential direction of the wrist W, the tip end portion 43 is engaged with the basal end portion 41 with a hook and loop fastener 45 which is formed on the surfaces of the basal end portion 41 and tip end portion 43 of the band 40.

The hook and loop fastener 45 is an engagement member for causing the tip end portion 43 to detachably engage with the basal end portion 41.

Incidentally, a configuration may be employed where, in the state shown in FIG. 2, a convex portion or concave portion which is disposed on the surface of the tip end portion 43 and directed to the housing 20 is fitted into a concave portion or convex portion which is disposed on the surface of the basal end portion 41 and directed in the direction opposite to the housing 20, whereby the tip end portion 43 is detachably engaged with the basal end portion 41. In this case, the concave portion and the convex portion constitute the engagement member.

An example of a method of attaching the thus configured biometric information measurement device 10 to the wrist W will be described.

Firstly, the measurement subject makes the basal end portion 41 of the band 40 pass through the hole portion 31 of the first engaging portion 29 of the housing 20 from the side of the detection surface 21 toward the display surface 23. Then, the measurement subject makes the basal end portion 41 which has passed through the hole portion 31, to be folded back in the direction to be separated from the housing 20 to be engaged with the band 40 through the hook and loop fastener 42. As a result, the basal end portion 41 is engaged with the first engaging portion 29.

Next, the measurement subject makes the tip end portion 43 of the band 40 pass through the hole portion of the second engaging portion 27 of the housing 20 from the side of the detection surface 21 toward the display surface 23, and folds back the band 40 which has passed through the hole portion of the second engaging portion 27, in the direction to be separated from the housing 20. As a result, the arbitrary position 44 of the band 40 is engaged with the second engaging portion 27. In this state, the measurement subject makes the arm pass through a space interposed between a portion between the basal end portion 41 and arbitrary position 44 of the band 40, and the detection surface 21.

After the measurement subject positions the housing 20 so that the pulse wave detecting section 22 is opposed to the radial artery TD, then, the measurement subject wounds the tip end portion 43 of the band 40 around the wrist W, and pulls up the tip end portion 43 to the vicinity of the first end portion 28 while directing from the hand back side to the palm side, i.e., from the side of the detection surface 21 toward the display surface 23.

The measurement subject adjusts the force of pulling the tip end portion 43 of the band 40, so as to cause the housing 20 to be in close contact with the wrist W at an adequate pressure. In this state, the measurement subject makes the tip end portion 43 of the band 40 overlap with the basal end portion 41 engaged with the first engaging portion 29 to be engaged with the basal end portion 41 through the hook and loop fastener 42.

At this time, the tip end portion 43 of the band 40 is engaged in a state where the tip end is directed from the detection surface 21 of the housing 20 toward the display surface 23. In other words, the tip end portion 43 of the band 40 is engaged with the basal end portion 41 in a state where the position of the tip end of the tip end portion 43 in a direction in which the detection surface 21 and display surface 23 of the housing 20 are juxtaposed (the vertical direction in FIG. 2) is on the side of the display surface 23 with respect to the position of the detection surface 21 of the housing 20 in this direction.

According to the biometric information measurement device 10, as described above, the tip end portion 43 of the band 40 is engaged in the state where the tip end is directed from the side of the detection surface 21 of the housing 20 toward the display surface 23. Therefore, a force which is applied to the wrist W when the band 40 is pulled is facilitated to evenly act on the side of the thumb and on the side of the little finger, and it is possible to prevent positional displacement of the pulse wave detecting section 22 from being caused. The attachment of the biometric information measurement device 10 can be performed while the back of the hand on a table remains to be opposed to the table surface. Therefore, it is possible to prevent positional displacement of the pulse wave detecting section 22 due to a motion of raising the hand from the table, from occurring.

According to the biometric information measurement device 10, as shown in FIG. 2, the housing 20 is secured to the wrist W in the state where the band 40 is doubly wound around the wrist W. In this manner, the wrist W can be covered by the double portions of the band 40, and therefore it is possible to prevent positional displacement of the housing 20 from occurring after attachment of the biometric information measurement device 10.

During attachment of the biometric information measurement device 10, the band 40 can be fastened in the state where the wrist W is inserted into the space interposed between the housing 20 and the band 40, and the housing 20 is positioned. As compared with the case where the band 40 is singly wound, therefore, the biometric information measurement device 10 can be easily attached. Moreover, the accuracy of positioning the pulse wave detecting section 22 can be improved.

Preferably, a configuration may be employed where the friction coefficient of the surface of the band 40 opposite to the side which is in contact with the wrist W is smaller than that of the surface on the side which is in contact with the wrist W.

According to the configuration, when the band 40 which is folded back in the second engaging portion 27 is to be wound around the wrist W, the band 40 easily slips over a portion of the band 40 which has been already wound around the wrist W. Therefore, the fastening manner of the band 40 can be easily adjusted, and the attachability and the accuracy of positioning the pulse wave detecting section 22 can be improved. With respect to the surface which is in contact with the wrist W, moreover, the band 40 and the wrist W hardly slip over each other, and therefore it is possible to prevent positional displacement of the housing 20 from occurring after attachment of the biometric information measurement device 10.

The biometric information measurement device 10 has the configuration where the first engaging portion 29 is disposed on the first end portion 28 and on the side of the display surface 23. According to the configuration, when the wrist W on a table is turned from a state where, for example, the back of the hand is directed to the table surface, toward the side of the little finger, the first engaging portion 29 is hardly contacted with the table surface. Therefore, a superior usability is obtained, and positional displacement of the pulse wave detecting section 22 can be prevented from occurring.

The biometric information measurement device 10 has the configuration where the basal end portion 41 of the band 40 is detachably engaged with the first engaging portion 29. According to the configuration, the band 40 can be completely detached from the housing 20. In the case where the band 40 is contaminated with human sweat or external environment (dust, scratch, or the like), therefore, this situation can be dealt with by replacement of the band 40.

The diameter and shape of the wrist of the measurement subject are different among individuals. When the band 40 is replaceable, a configuration may be possible where, for example, a plurality of kinds of bands 40 are selectively used in accordance with the measurement subject. As a result, regardless of individual variations, it is possible to realize superior attachability.

The biometric information measurement device 10 has the configuration where the basal end portion 41 of the band 40 is engaged with the first engaging portion 29 in the state where the basal end portion is folded back to be separated from the housing 20. According to the configuration, a work of detaching the band 40 from the housing 20 is easily performed, and the usability can be improved.

The biometric information measurement device 10 has the configuration where the tip end portion 43 of the band 40 is engaged with the basal end portion 41 on the side of the ulna S in the wrist W. The measurement subject performs a work of routing the band 40 with using the right hand. Therefore, the engagement of the tip end portion 43 of the band 40 can be performed on the side of the ulna S where the right hand exists, whereby attachment of the biometric information measurement device 10 can be easily performed.

The biometric information measurement device 10 has the configuration where the tip end portion 43 of the band 40 is engaged with the basal end portion 41 with the hook and loop fastener 45. According to the configuration, the function of the hook and loop fastener 45 facilitates adjustment of the winding force of the band 40. Therefore, the attachability can be improved.

Figure 4:
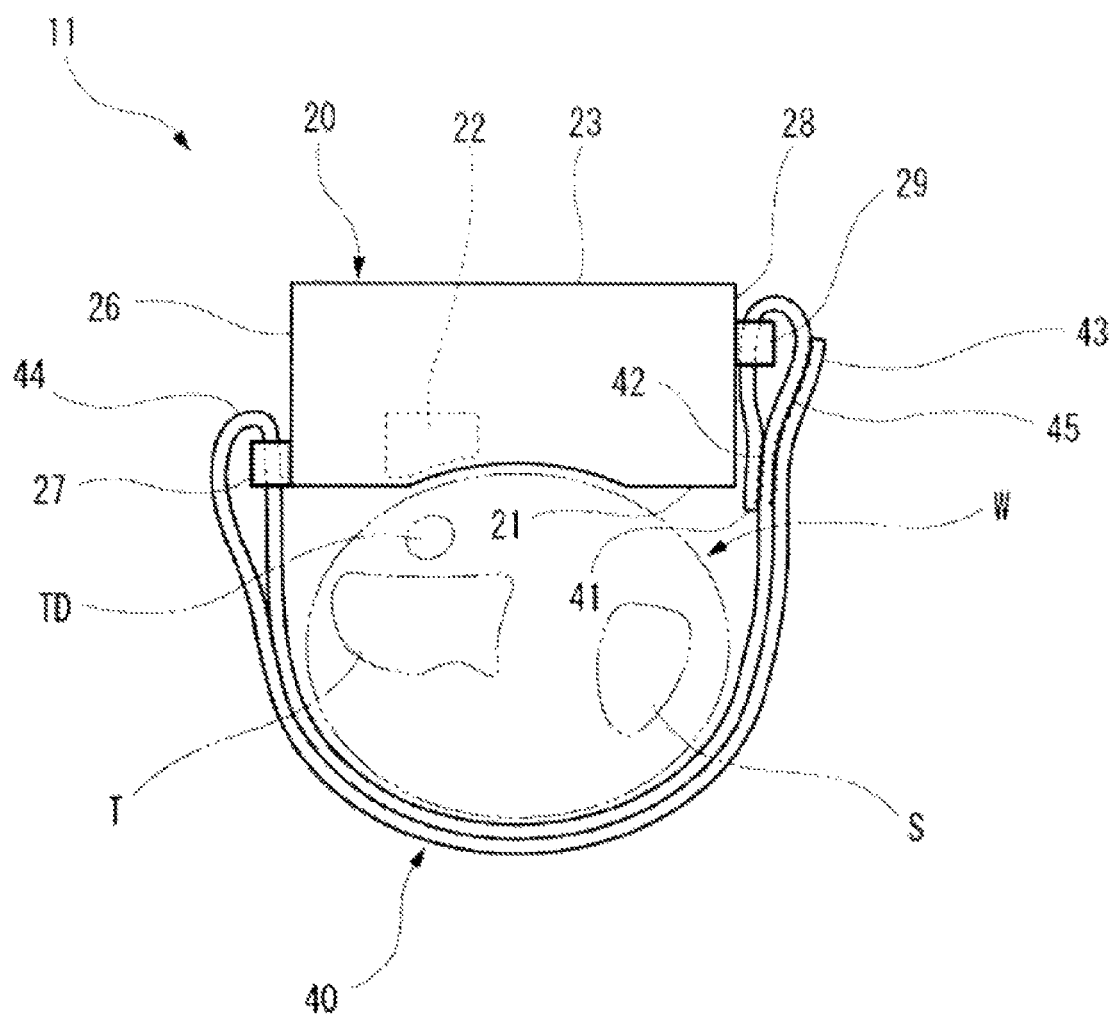
FIG. 4 is a side view of a biometric information measurement device 11 which is a modification of the biometric information measurement device 10 shown in FIG. 1, as seen from the side of the elbow of the left hand of the measurement subject.

FIG. 4 is a side view of a biometric information measurement device 11 which is a modification of the biometric information measurement device 10 shown in FIG. 1, as seen from the side of the elbow of the left hand of the measurement subject. In FIG. 4, portions which are in common with the biometric information measurement device 10 are denoted by the same reference numerals, and duplicated description is omitted.

In the biometric information measurement device 11, the folding-back direction of the basal end portion 41 of the band 40 is opposite to that in the biometric information measurement device 10. The tip end portion 43 of the band 40 is engaged on the surface which is in the non-folded back part of the basal end portion 41, and which is directed in the direction opposite to the housing 20. The other configuration is identical with that of the biometric information measurement device 10.

Specifically, the basal end portion 41 of the band 40 of the biometric information measurement device 11 passes through the hole portion 31 of the first engaging portion 29 which is disposed on the first end portion 28 of the housing 20, from the side of the display surface 23 toward the detection surface 21. Then, the folded back part of the basal end portion 41 is engaged with the non-folded back part of the basal end portion 41 with the hook and loop fastener 42.

The tip end portion 43 of the band 40 of the biometric information measurement device 11 is engaged with the basal end portion 41 with the hook and loop fastener 45, at a position where the portion overlaps with the first end portion 28 in the circumferential direction of the wrist W.

According to the biometric information measurement device 11, the part of the basal end portion 41 with which the tip end portion 43 of the band 40 is engaged has an approximately flat surface. Therefore, a work of attaching or detaching the tip end portion 43 can be easily performed.

The biometric information measurement device 11 has the configuration where the basal end portion 41 of the band 40 is engaged with the first engaging portion 29 in a state where the basal end portion is folded back in a direction approaching the housing 20. When the engagement state of the tip end portion 43 with respect to the basal end portion 41 is to be released, therefore, the engagement state between the parts of the basal end portion 41 is hardly released. Consequently, the engagement state of the basal end portion 41 with respect to the first engaging portion 29 can be stably maintained.

Figure 5:
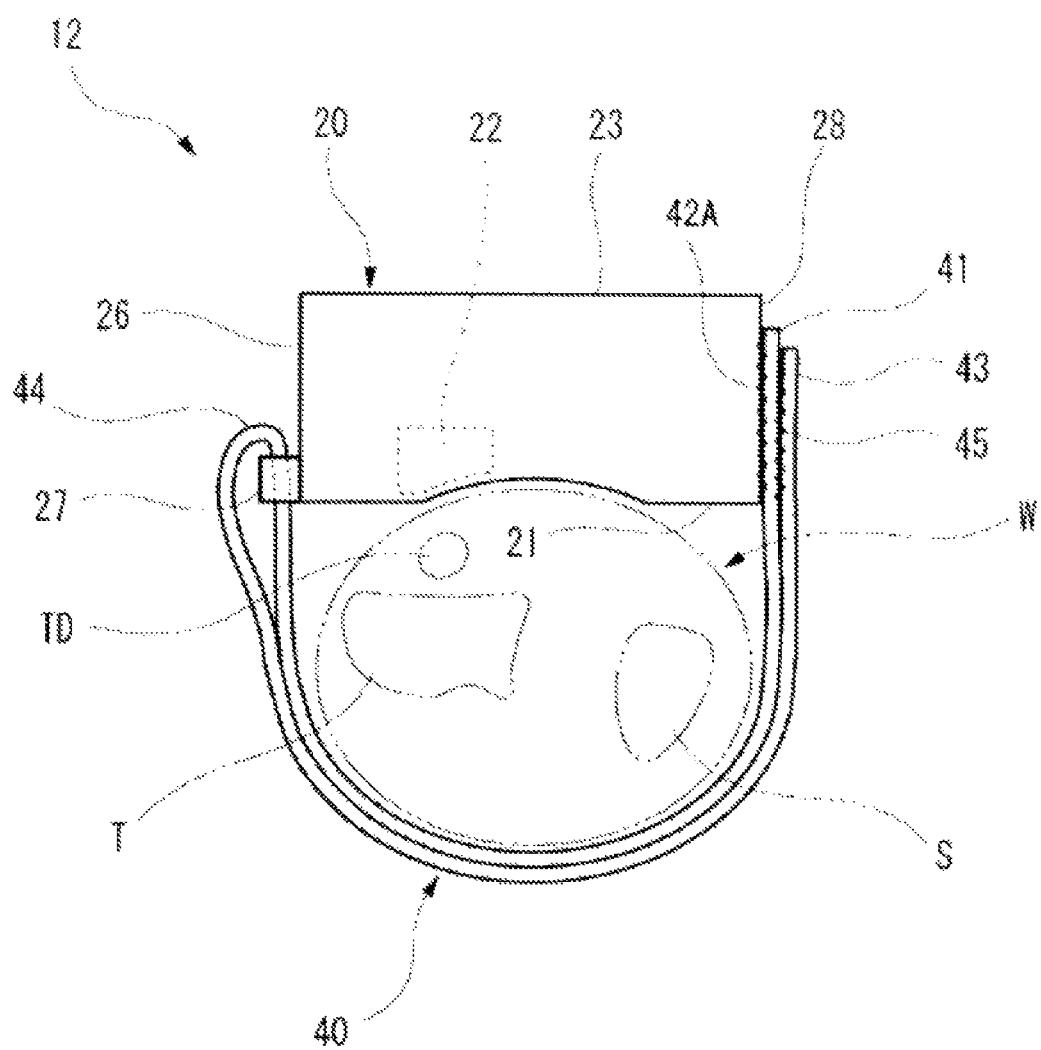
FIG. 5 is a side view of a biometric information measurement device 12 which is a modification of the biometric information measurement device 10 shown in FIG. 1, as seen from the side of the elbow of the left hand of the measurement subject.

FIG. 5 is a side view of a biometric information measurement device 12 which is a modification of the biometric information measurement device 10 shown in FIG. 1, as seen from the side of the elbow of the left hand of the measurement subject. In FIG. 5, portions which are in common with the biometric information measurement device 10 are denoted by the same reference numerals, and duplicated description is omitted.

In the biometric information measurement device 12, the above-described first engaging portion 29 is not disposed on the first end portion 28 of the housing 20. Instead, the basal end portion 41 of the band 40 of the biometric information measurement device 12 is engaged with the first end portion 28 through a hook and loop fastener 42A. In the biometric information measurement device 12, the hook and loop fastener 42A which is formed on the first end portion 28 constitutes the first engaging portion.

The hook and loop fastener 42A is an engagement member for detachably engaging the basal end portion 41 to the first end portion 28. Instead of the hook and loop fastener 42A, the above-described concavo-convex structure may be employed.

The tip end portion 43 of the band 40 of the biometric information measurement device 12 is detachably engaged through the hook and loop fastener 45 with the surface of the basal end portion 41 which is engaged with the first end portion 28, the surface being directed in the direction opposite to the housing 20.

The other configuration is similar to that of the biometric information measurement device 10.

According to the biometric information measurement device 12, the part of the basal end portion 41 with which the tip end portion 43 of the band 40 is engaged has an approximately flat surface. Therefore, a work of attaching or detaching the tip end portion 43 can be easily performed.

In the biometric information measurement device 12, alternatively, the basal end portion 41 may be non-detachably engaged with the first end portion 28 by adhesion, screws, or the like. According to the configuration, the engagement state of the basal end portion 41 can be stably maintained.

Figure 6:
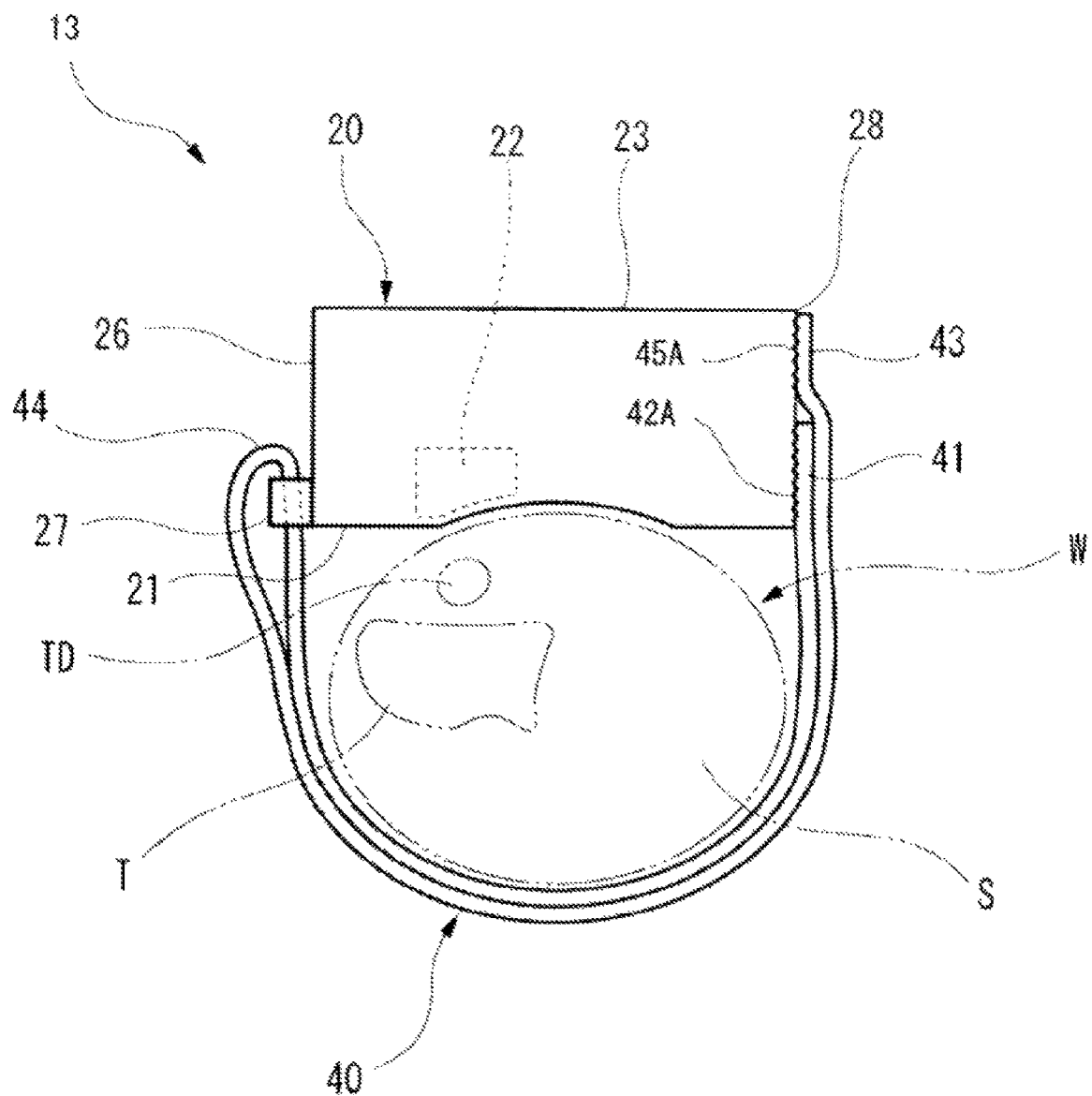
FIG. 6 is a side view of a biometric information measurement device 13 which is a modification of the biometric information measurement device 10 shown in FIG. 1, as seen from the side of the elbow of the left hand of the measurement subject.

FIG. 6 is a side view of a biometric information measurement device 13 which is a modification of the biometric information measurement device 10 shown in FIG. 1, as seen from the side of the elbow of the left hand of the measurement subject. In FIG. 6, portions which are in common with those of the biometric information measurement device 12 are denoted by the same reference numerals, and duplicated description is omitted.

The biometric information measurement device 13 is configured in the same manner as the biometric information measurement device 12 shown in FIG. 5 except that the tip end portion 43 of the band 40 is engaged with the first end portion 28 of the housing 20 with a hook and loop fastener 45A.

The tip end portion 43 of the band 40 of the biometric information measurement device 13 is engaged with the first end portion 28 with the hook and loop fastener 45A in a state where the tip end portion overlaps with the basal end portion 41 in the circumferential direction of the wrist W.

The hook and loop fastener 45A is an engagement member for causing the tip end portion 43 to detachably engage with the first end portion 28. Instead of the hook and loop fastener 45A, the above-described concavo-convex structure may be employed.

The biometric information measurement device 13 can attain effects similar to those of the biometric information measurement device 12. According to the biometric information measurement device 13, when the engagement state of the tip end portion 43 with respect to the housing 20 is to be cancelled, it is possible to easily prevent the engagement state between the basal end portion 41 and the housing 20 from being cancelled.

The biometric information measurement device 13 may be configured so that the hook and loop fastener 45A is extended onto the display surface 23, and the tip end portion 43 of the band 40 is engaged with the housing 20 by two surfaces or the end surface of the housing 20 and the display surface 23. According to the configuration, it is possible to prevent the vicinity of the tip end of the tip end portion 43 from being in a free state, and the beauty of the device can be improved. Moreover, it is possible to prevent the tip end portion 43 of the band 40 from peeling off after attachment of the biometric information measurement device 10.

Figure 7:
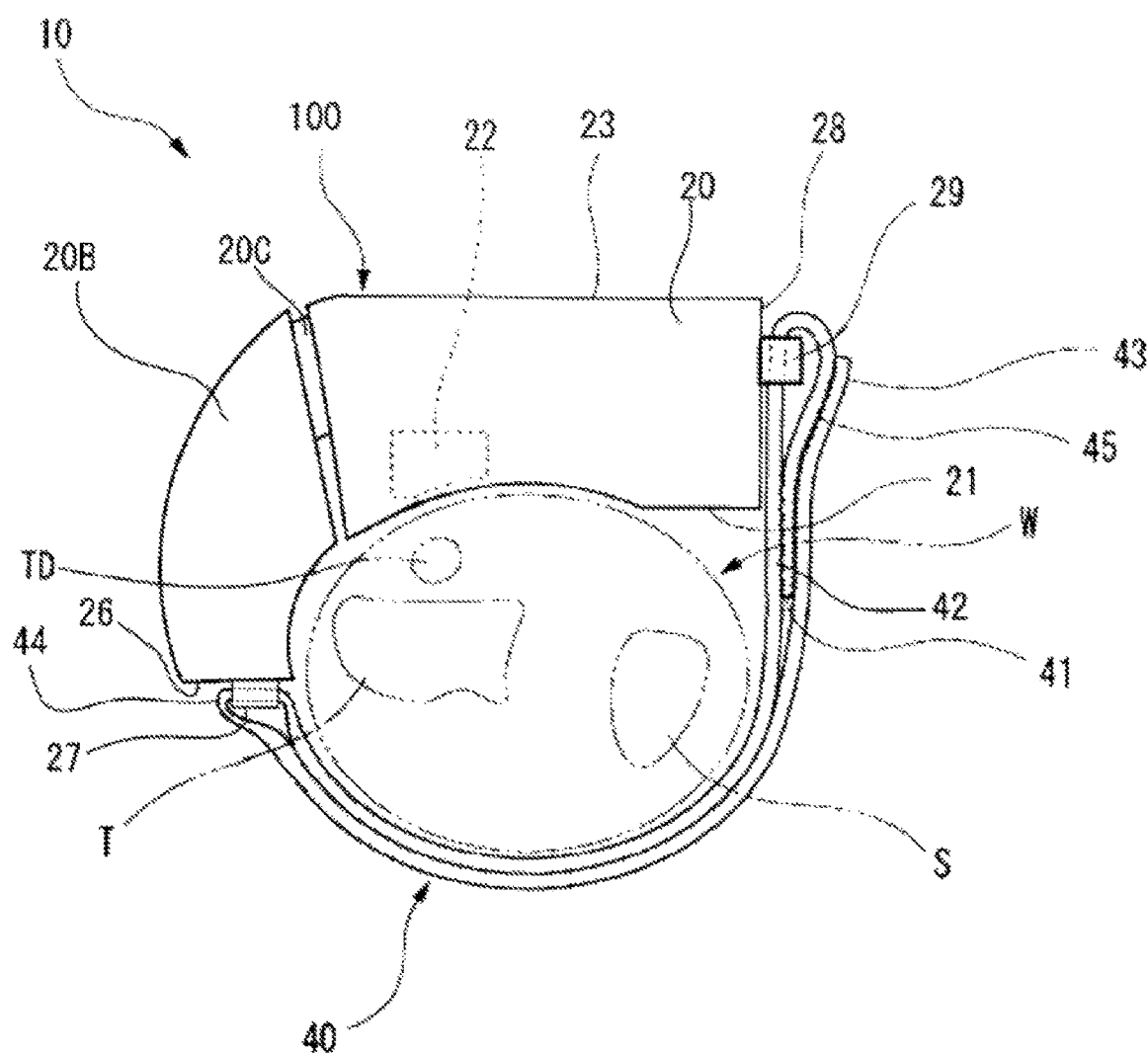
FIG. 7 is a view showing a modification of a body portion of the biometric information measurement device 10 shown in FIG. 1.

Although the examples in which the body portion of the biometric information measurement device 10 is configured by the single housing 20 have been described, the configuration is not limited thereto. FIG. 7 is a view showing a modification of the body portion of the biometric information measurement device 10. In FIG. 7, configurations which are identical with those of FIG. 2 are denoted by the same reference numerals.

The body portion 100 of the biometric information measurement device 10 shown in FIG. 7 is configured by: the above-described housing 20; a housing 20B; and a coupling portion 20C which swingably couples together the housing 20 and the housing 20B, such as a hinge. In the example of FIG. 7, for example, the housing 20B accommodates batteries or the like for driving the biometric information measurement device 10.

The body portion 100 has a longitudinal shape which extends along the circumferential direction of the wrist, as a whole, and a shape which is opened at least on the side of the ulna S in the wrist. The body portion 100 has a configuration where, in a state where the body portion is attached to the wrist with the band 40, the portion between the end portions in the circumferential direction of the wrist does not cover the wrist at a degree that a part of the band 40 is in contact with the wrist.

In the example of FIG. 7, an end portion which is one of the end portions of the housing 20B on the side opposite to the housing 20 in the circumferential direction of the wrist constitutes the above-described second end portion 26, and the second engaging portion 27 is formed on the second end portion 26.

The above-disclosed embodiment should be considered in all respects to be illustrative and not restrictive. The scope of the present invention is represented by the appended claims rather than the foregoing description, and all changes within the meaning and range of equivalents thereof are intended to be covered therein.

As described above, the following matters are disclosed in the specification.

The disclosed pulse wave detector is used while being attached to a wrist of a measurement subject and includes: a body portion which includes a detecting section configured to detect a pulse wave from a radial artery of the measurement subject; a band which is configured to be wound around the wrist in a state where the band is engaged with the body portion, so as to maintain a state where the detecting section is opposed to the radial artery; a first engaging portion which is disposed on a first end portion that is one of end portions of the body portion on a side of an ulna of the wrist in a circumferential direction of the wrist, and with which a basal end portion in a longitudinal direction of the band is engaged; a second engaging portion which is disposed on a second end portion that is one of the end portions of the body portion on a side of a radius of the wrist in the circumferential direction, and with which an arbitrary position in the longitudinal direction of the band engaged with the first engaging portion is engaged in a state where the band is folded back in a direction to be separated from the body portion; and an engagement member which is configured to cause a tip end portion in the longitudinal direction of the band to be engaged with the basal end portion or the first end portion in a state where the basal end portion engaged with the first engaging portion and the tip end portion of the band engaged with the second engaging portion overlap with each other, wherein the tip end portion is engaged with the basal end portion or the first end portion through the engagement member in a state where a tip end of the tip end portion is directed from a side of an opposed surface of the body portion to the wrist, to a side of a surface of the body portion which is opposite to the opposed surface.

In the disclosed pulse wave detector, the first engaging portion includes a Π-shaped member with which the basal end portion is engaged in a folded back state and disposed on the first end portion and on the side of the opposite surface.

In the disclosed pulse wave detector, the basal end portion of the band is folded back in the first engaging portion to be stacked and a stacked state is releasable.

In the disclosed pulse wave detector, the basal end portion of the band is engaged in a state of being folded back in a direction to be separated from the first end portion.

In the disclosed pulse wave detector, the detecting section is configured to detect a pressure pulse wave from the radial artery by using a pressure detecting element.

The disclosed biometric information measurement device includes: the above pulse wave detector; and a biometric information calculating section which is configured to calculate biometric information based on the pulse wave detected by the detecting section.

Accordingly, it is possible to provide a pulse wave detector which can accurately detect a pulse wave while realizing superior attachability and preventing positional displacement of a pulse wave detecting section with respect to the radial artery from occurring, and also a biological information measurement device including the detector.

The pulse wave detector of the present invention is effective particularly in application to a portable blood pressure monitor or the like.

Although the present invention has been described with reference to the specific embodiment, the present invention is not limited to the embodiment, and various changes can be made without departing from the technical concept of the disclosed invention.

The invention claimed is:

1. A pulse wave detector which is used while being attached to a wrist of a measurement subject, the pulse wave detector comprising:
   a body portion which includes a detecting section disposed in a position which is opposed to a radial artery of the measurement subject and configured to detect a pulse wave from the radial artery;
   a band which is configured to be wound around the wrist in a state where the band is engaged with the body portion;
   a first engaging portion which is disposed on a first end portion of the body portion in a circumferential direction of the wrist, and with which a basal end portion in a longitudinal direction of the band is engaged;
   a second engaging portion which is disposed on a second end portion of the body portion that is opposite to the first end portion, and with which an arbitrary position in the longitudinal direction of the band engaged with the first engaging portion is engaged in a state where the band is folded back in a direction to be separated from the body portion; and
   an engagement member which is configured to engage a tip end portion in the longitudinal direction of the band with the basal end portion or the first end portion in a state where the basal end portion engaged with the first engaging portion and the tip end portion of the band engaged with the second engaging portion overlap with each other,
   wherein the tip end portion is engaged with the basal end portion or the first end portion through the engagement member in a state where a tip end of the tip end portion is directed from a side of the detection surface to a side of the opposite surface,
wherein the first engaging portion is disposed on the first end portion at a position closer to an opposite surface of the body portion which is opposite to a detection surface of the body portion that is opposed to the wrist than the detection surface,
wherein the second engaging portion is disposed on the second end portion at a position closer to the detection surface than the opposite surface of the body portion, and
wherein the first engaging portion and the second engaging portion are respectively disposed on the first end portion and the second portion to be equidistant from a virtual line halving the body portion in a direction perpendicular to the detection surface.

2. The pulse wave detector according to claim 1,
wherein the first engaging portion includes a Π-shaped member with which the basal end portion is engaged in a folded back state.

3. The pulse wave detector according to claim 1,
wherein the basal end portion of the band is folded back in the first engaging portion to be stacked in a stacked state and the stacked state is releasable.

4. The pulse wave detector according to claim 3,
wherein the basal end portion of the band is engaged in a state of being folded back in a direction to be separated from the first end portion.

5. The pulse wave detector according to claim 1,
wherein the detecting section is configured to detect a pressure pulse wave from the radial artery by using a pressure detecting element.

6. A biometric information measurement device comprising:
the pulse wave detector according to claim 1; and
a biometric information calculating section which is configured to calculate biometric information based on the pulse wave detected by the detecting section.

* * * * *